(12) United States Patent
Hasegawa

(10) Patent No.: US 10,627,337 B2
(45) Date of Patent: Apr. 21, 2020

(54) CELL SURVIVAL RATE DETERMINING DEVICE AND CELL SURVIVAL RATE DETERMINING METHOD

(71) Applicant: AZBIL CORPORATION, Chiyoda-ku (JP)

(72) Inventor: Norio Hasegawa, Chiyoda-ku (JP)

(73) Assignee: AZBIL CORPORATION, Chiyoda-ku (JP)

( * ) Notice: Subject to any disclaimer, the term of this patent is extended or adjusted under 35 U.S.C. 154(b) by 210 days.

(21) Appl. No.: 15/955,982

(22) Filed: Apr. 18, 2018

(65) Prior Publication Data

US 2018/0306703 A1 Oct. 25, 2018

(30) Foreign Application Priority Data

Apr. 19, 2017 (JP) .................................. 2017-082675

(51) Int. Cl.
*G06T 7/00* (2017.01)
*G01N 15/00* (2006.01)
(Continued)

(52) U.S. Cl.
CPC ............... *G01N 21/17* (2013.01); *C12M 1/00* (2013.01); *C12M 41/46* (2013.01);
(Continued)

(58) Field of Classification Search
CPC ............... G06T 7/0012; G06T 7/0014; G06T 2207/30024; G06T 2207/30242; G06K 9/00127; G06K 9/00247; C12M 41/46; G01N 2015/0053; G01N 2015/0065; G01N 15/02; G01N 15/0205; G01N 15/0227; G01N 15/1434; G01N 15/1481; G01N 21/17; G01N 21/1744
See application file for complete search history.

(56) References Cited

U.S. PATENT DOCUMENTS 5,162,204 A * 11/1992 Matsuzaki et al. .... C12M 41/36
435/286.1
2019/0331581 A1* 10/2019 Ikehata et al. ......... C12M 41/06

FOREIGN PATENT DOCUMENTS

JP 2-27977 A 1/1990
JP 2592114 B2 3/1997
(Continued)

OTHER PUBLICATIONS

Korean Office Action dated Sep. 27, 2019 in Patent Application No. 10-2018-0045033 (with English translation), 9 pages.

*Primary Examiner* — Andrew W Johns
(74) *Attorney, Agent, or Firm* — Oblon, McClelland, Maier & Neustadt, L.L.P.

(57) ABSTRACT

A cell survival rate determining device includes a distribution acquisition unit acquiring a particle size distribution in a solution containing particles including cultured cells; a classification unit classifying the particles into a small particle group and a large particle group using a predetermined threshold in the distribution; a ratio calculation unit calculating the value of a ratio between the number of particles belonging to the small particle group and the number of particles belonging to the large particle group; and a survival rate determination unit determining the survival rate of the cultured cells from the value of the ratio using a pre-acquired relationship between the ratio and cell survival rate.

10 Claims, 10 Drawing Sheets

(51) Int. Cl.
G01N 21/17 (2006.01)
G01N 15/14 (2006.01)
G01N 15/02 (2006.01)
C12M 1/00 (2006.01)
C12M 1/34 (2006.01)
*G01N 21/01* (2006.01)

(52) U.S. Cl.
CPC ..... *G01N 15/0227* (2013.01); *G01N 15/1434* (2013.01); *G06T 7/0016* (2013.01); *G01N 2015/0053* (2013.01); *G01N 2015/0065* (2013.01); *G01N 2015/1481* (2013.01); *G01N 2021/0112* (2013.01); *G01N 2021/0181* (2013.01); *G01N 2021/0193* (2013.01); *G01N 2021/1744* (2013.01)

(56) References Cited

FOREIGN PATENT DOCUMENTS

JP          4868879 B2     2/2012
JP          2016-5437 A    1/2016

\* cited by examiner $y = -0.1038x + 11.169$

CELL SURVIVAL RATE DETERMINING DEVICE AND CELL SURVIVAL RATE DETERMINING METHOD

CROSS-REFERENCE TO RELATED APPLICATIONS

The present application is based on and claims priority to Japanese Application No. 2017-082675, filed Apr. 19, 2017, the entire contents of which are incorporated herein by reference.

BACKGROUND

1. Field

The present disclosure relates to a cell culture technique and relates to a cell survival rate determining device and a cell survival rate determining method.

2. Description of the Related Art

In the fields of bioprocess and cell culture, for example, in order to control the conditions of cell culture and judge the time of stopping cell culture, the life or death of cultured cells is determined to measure the survival rate. As a method for determining the life or death of cells, proposed is a method of coupling a fluorescent dye to a nucleic acid in a cell and determining the life or death of the cell by the intensity of excited fluorescence (for example, see Japanese Patent No. 2592114). There is known a method for determining the life or death of cells by staining with trypan blue that permeates through the cell membrane of dead cells and stains the cytoplasm of the dead cells blue.

However, staining reagents are expensive, and the process of staining cells is complicated. In addition, the staining reagents are often harmful to human bodies. Accordingly, the storage of staining reagents is required to be managed. In addition, it is difficult to subsequently culture the cells stained with a staining reagent, and it is also necessary to carefully treat the waste fluid. In contrast, a method for determining the life or death of cells based on the autofluorescence emitted by the cells, without using a staining reagent, has been proposed (for example, see Japanese Patent No. 4868879).

SUMMARY

Since the autofluorescence emitted by cells is weak, a long exposure time may be required, or a high-sensitive fluorescence detector may be needed. Accordingly, it is an object of the present disclosure to provide a cell survival rate determining device and a cell survival rate determining method that can determine the survival rate of cells without using a staining reagent and without depending on the autofluorescence of cells.

According to an aspect of the present disclosure, provided is a cell survival rate determining device including a distribution acquisition unit acquiring a particle size distribution in a solution containing particles including cultured cells; a classification unit classifying the particles into a small particle group and a large particle group using a predetermined threshold in the distribution; a ratio calculation unit calculating the value of a ratio between the number of particles belonging to the small particle group and the number of particles belonging to the large particle group; and a survival rate determination unit determining the survival rate of the cultured cells from the value of the ratio using a pre-acquired relationship between the ratio and cell survival rate.

In the cell survival rate determining device, the distribution acquisition unit may acquire a particle size distribution based on an image of a solution.

In the cell survival rate determining device, the distribution acquisition unit may acquire a particle size distribution based on the intensity of scattered light generated in each of the particles.

The cell survival rate determining device may further include a detachable flow channel in which a solution flows, a detachable measuring cuvette connected to the flow channel, an irradiator irradiating the inside of the measuring cuvette with measurement light, and a scattered light measuring device measuring the intensity of scattered light generated in the measuring cuvette irradiated with the measurement light.

In the cell survival rate determining device, the cultured cells may be suspension-cultured.

In the cell survival rate determining device, the cultured cells may be Chinese hamster ovary (CHO) cells.

According to another aspect of the present disclosure, provided is a cell survival rate determining method including acquiring a particle size distribution in a solution containing particles including cultured cells; classifying the particles into a small particle group and a large particle group using a predetermined threshold in the distribution; calculating the value of a ratio between the number of particles belonging to the small particle group and the number of particles belonging to the large particle group; and determining the survival rate of the cultured cells from the value of the ratio using a pre-acquired relationship between the ratio and cell survival rate.

In the cell survival rate determining method, the particle size distribution may be acquired based on an image of a solution.

In the cell survival rate determining method, the particle size distribution may be acquired based on the intensity of scattered light generated in each of the particles.

The cell survival rate determining method may further include allowing a solution to flow in a detachable flow channel and a detachable measuring cuvette connected to the flow channel, irradiating the inside of the measuring cuvette with measurement light, and measuring the intensity of scattered light generated in the measuring cuvette irradiated with the measurement light.

In the cell survival rate determining method, the cultured cells may be suspension-cultured.

In the cell survival rate determining method, the cultured cells may be Chinese hamster ovary (CHO) cells.

The present disclosure can provide a cell survival rate determining device and a cell survival rate determining method that can determine the survival rate of cells without using a staining reagent and without depending on the autofluorescence of cells.

DETAILED DESCRIPTION

Embodiments of the present disclosure will now be described. In the following description of the drawings, the same or similar portions are denoted by the same or similar reference signs. However, the drawings are schematic. Accordingly, the specific dimensions and the like should be determined by considering the following description. It should be also noted that the drawings may include portions which differ from one drawing to another in dimensional relationship and ratios.

It should not be understood that the description and drawings constituting a part of this disclosure limit the present disclosure. From this disclosure, various alternative embodiments, examples, and operational techniques will be apparent to those skilled in the art. Accordingly, it should be understood that the present disclosure encompasses various embodiments and the like not described herein.

First Embodiment

Figure 1:
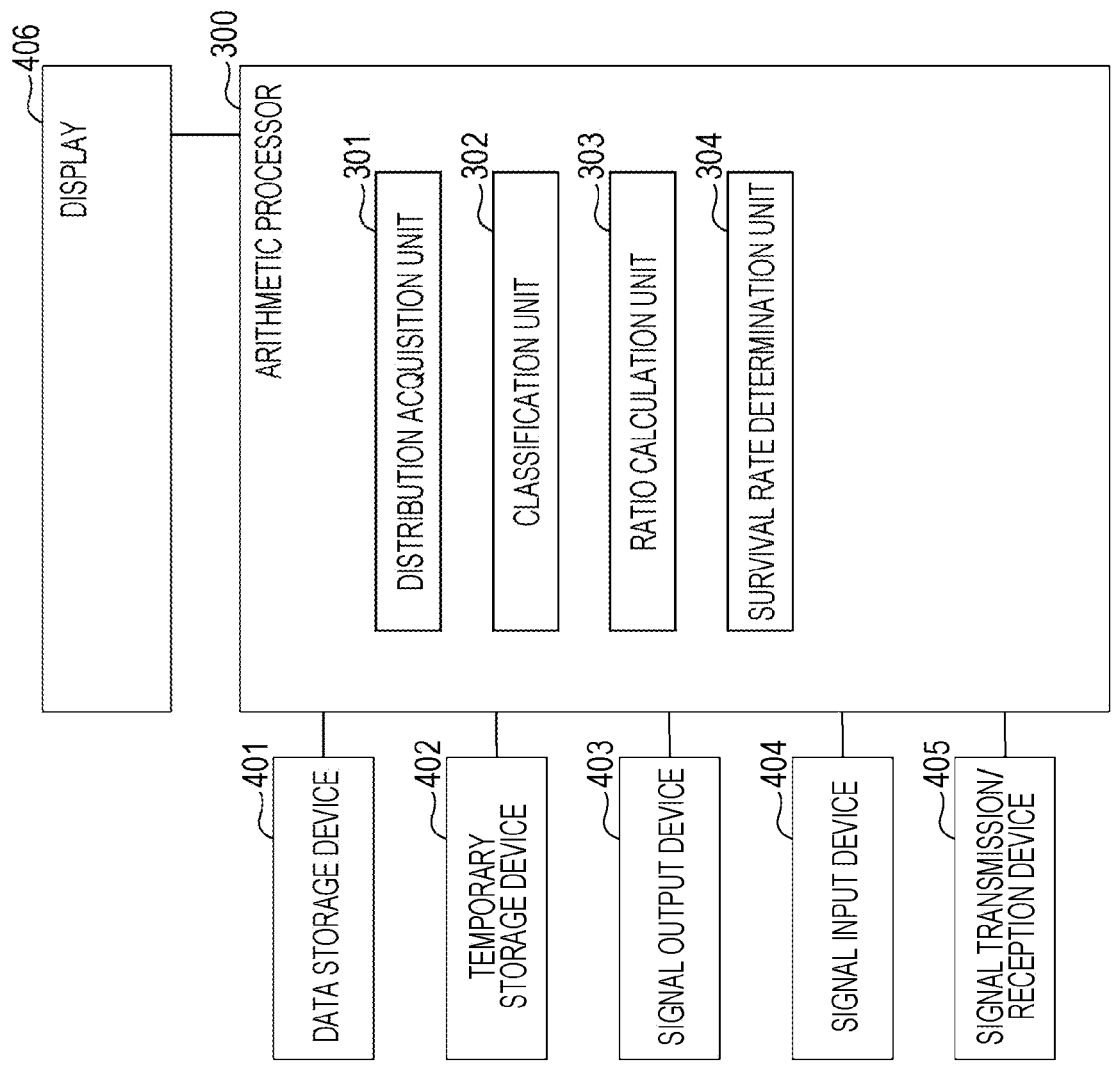
FIG. 1 is a schematic diagram of a cell survival rate determining device according to a first embodiment.
Figure 2:
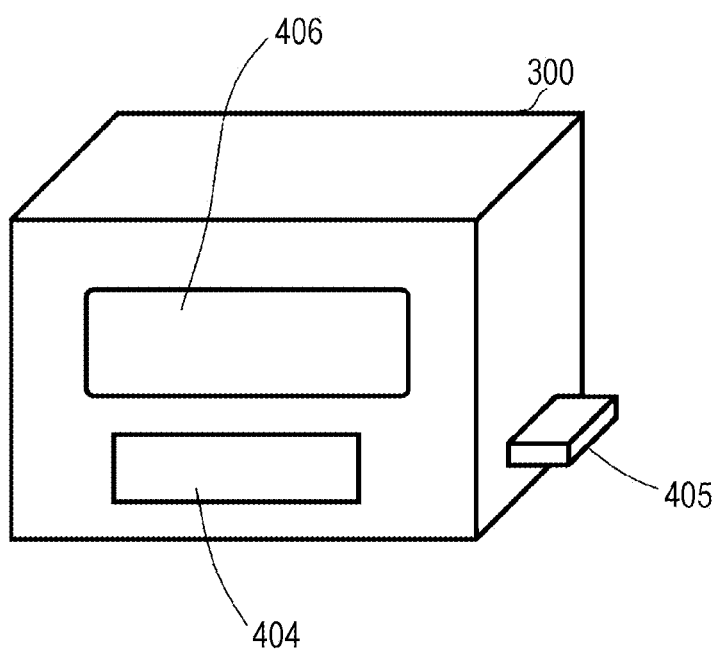
FIG. 2 is a schematic diagram of a cell survival rate determining device according to the first embodiment.

The cell survival rate determining device according to a first embodiment, as shown in FIGS. 1 and 2, includes a distribution acquisition unit 301 acquiring a particle size distribution in a solution containing particles including cultured cells; a classification unit 302 classifying the particles into a small particle group and a large particle group using a predetermined threshold in the distribution; a ratio calculation unit 303 calculating the value of a ratio between the number of particles belonging to the small particle group and the number of particles belonging to the large particle group; and a survival rate determination unit 304 determining the survival rate of the cultured cells from the value of the ratio using a pre-acquired relationship between the ratio and cell survival rate. The distribution acquisition unit 301, the classification unit 302, the ratio calculation unit 303, and the survival rate determination unit 304 are included in, for example, an arithmetic processor 300.

The cultured cells are, for example, suspension-cultured cells. In suspension culture, spherical cells grow in a state of floating in a culture medium without adhering to the bottom of the incubator. The cultured cells may be adherent cultured cells. Examples of the cultured cells include all kinds of cells. For example, the cultured cells are antibody-producing cells. Examples of the antibody-producing cells include Chinese hamster ovary (CHO) cells. The term "CHO cell" includes established CHO cell lines. In addition, the term "CHO cell" includes subspecies, such as CHO-K1 cells and dihydrofolate reductase (DHFR) deficient CHO-DG44 cells.

The distribution acquisition unit 301 acquires a frequency distribution of particle size per unit volume based on, for example, an image of a solution containing particles including cultured cells. The frequency distribution of particle size is acquired by measuring the sizes of individual particles in an image of a solution containing particles including cultured cells. The image of a solution containing particles including cultured cells is an image of a solution containing suspension-cultured cells. Alternately, the image of a solution containing particles including cultured cells is an image of a solution containing adherent cultured cells detached from the incubator and suspended in a solution. The frequency distribution of particle size is represented by, for example, a histogram. However, the frequency distribution of particle size need not be necessarily represented visually.

The size of particles including cultured cells may be the diameter of the particles or the radius of the particles. A numerical value reflecting the size of particles may be used as an index representing the particle size. For example, irradiation of particles with light generates Mie scattered light in the particles. The intensity of the Mie scattered light reflects the size of the particles. Accordingly, the intensity of Mie scattered light may be used as an index representing the size of particles. In such a case, the distribution acquisition unit 301 acquires a particle size distribution based on the intensity of scattered light generated in each of the particles.

Figure 3A:
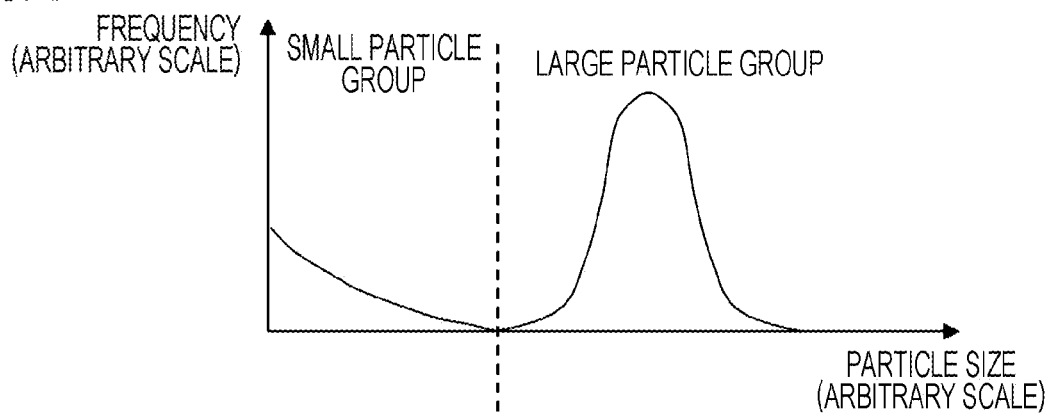
FIGS. 3A to 3C are schematic graphs showing frequency distributions of particles according to the first embodiment.
Figure 3B:
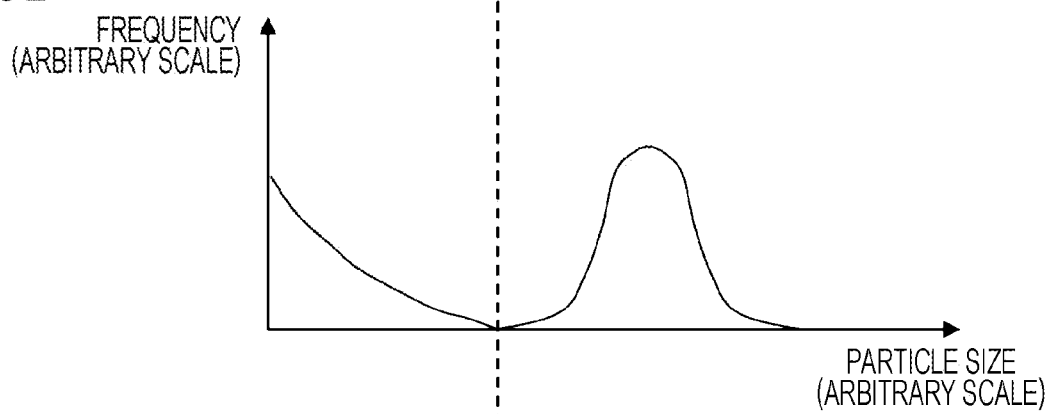
Figure 3C:
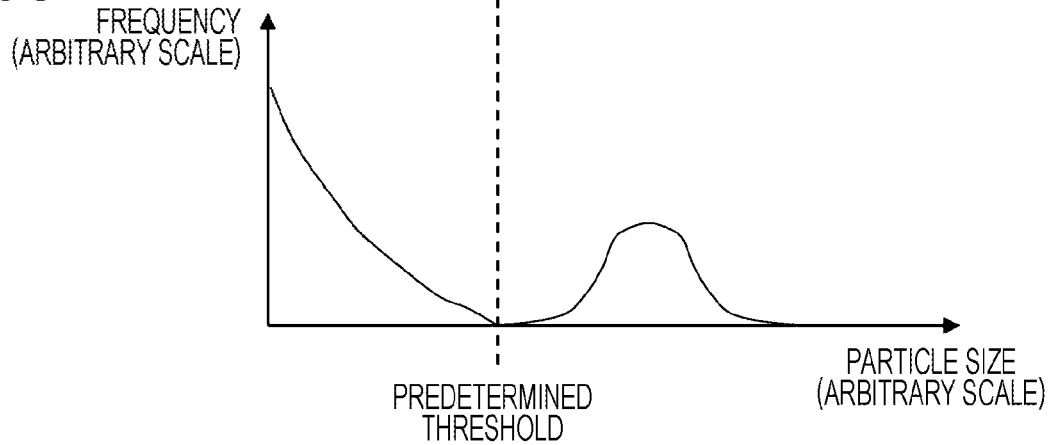

According to the findings by the present inventor, when the size of particles in a solution containing particles including cultured cells is measured, as shown in FIG. 3A, a large particle group of particles having a size larger than a predetermined threshold and a small particle group of particles having a size smaller than the predetermined threshold are observed. When the number of dead cells in the culture medium increases with an increase in the number of days of cell culture, as shown in FIG. 3B, there is a tendency that the number of particles belonging to the large particle group decreases and the number of particles belonging to the small particle group increases, compared to that in the initial stage of the culture. When the number of dead cells in the culture medium further increases with a further increase in the number of days of cell culture, as shown in FIG. 3C, there is a tendency that the number of particles belonging to the large particle group further decreases, and the number of particles belonging to the small particle group further increases.

Figure 4:
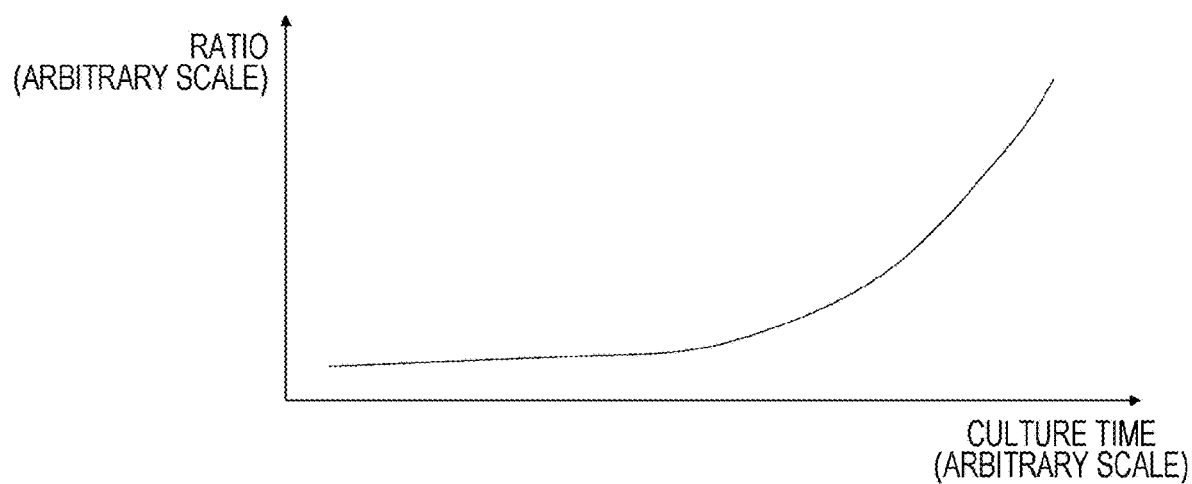
FIG. 4 is a schematic graph showing a relationship between the culture time of cells and the ratio of the number of particles belonging to the small particle group to the number of particles belonging to the large particle group according to the first embodiment.
Figure 5:
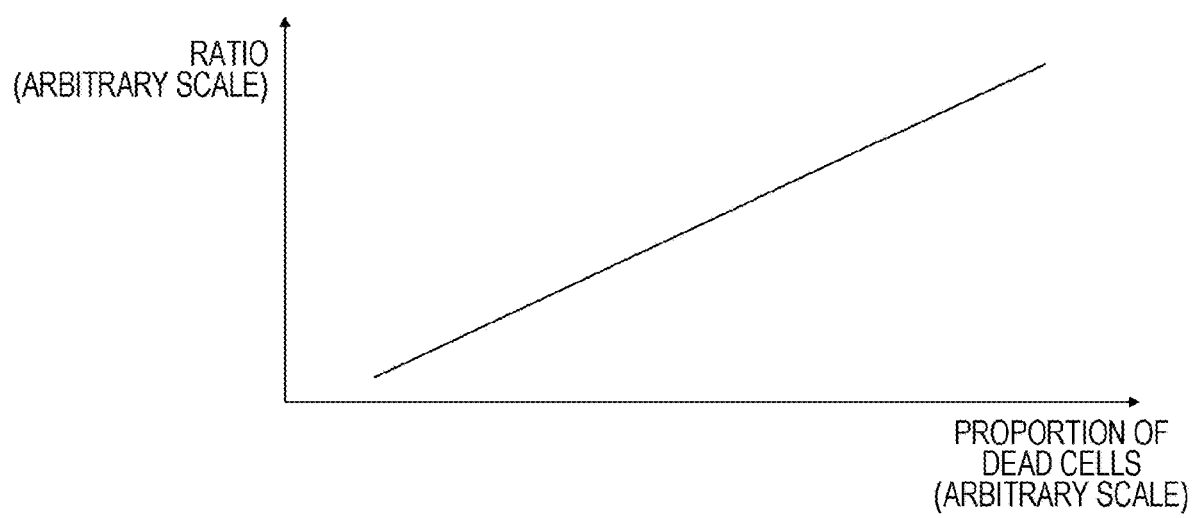
FIG. 5 is a schematic graph showing a relationship between the proportion of dead cells and the ratio of the number of particles belonging to the small particle group to the number of particles belonging to the large particle group according to the first embodiment.

Accordingly, for example, as shown in FIG. 4, the ratio of the number of particles belonging to the small particle group to the number of particles belonging to the large particle group tends to increase as the culture time increases. In addition, as shown in FIG. 5, the ratio of the number of particles belonging to the small particle group to the number of particles belonging to the large particle group tends to increase as the proportion of dead cells in the solution increases.

The relationship between the ratio of the number of particles belonging to the small particle group to the number of particles belonging to the large particle group and the proportion of dead cells or living cells in a solution can be acquired in advance. For example, the ratio of the number of particles belonging to the small particle group to the number of particles belonging to the large particle group in a solution containing cells is measured every day from the start of cell culture, and the proportion of dead cells or living cells in the solution containing cells is measured by a known method, such as trypan blue staining. Thus, a relationship between the ratio of the number of particles belonging to the small particle group to the number of particles belonging to the large particle group and the proportion of dead cells or living cells in the solution is acquired. In the acquisition of the relationship, an approximation method, such as a least-squares method, may be appropriately adopted. For example, the relationship may be represented by a linear function with the ratio as an independent variable and the proportion as a dependent variable.

The arithmetic processor 300 shown in FIG. 1 is connected to, for example, a data storage device 401. The data storage device 401 stores a relationship between the ratio of the number of particles belonging to the small particle group to the number of particles belonging to the large particle group and the proportion of dead cells or living cells in a solution previously acquired as described above.

The classification unit 302 classifies the particles in the frequency distribution of particle size acquired by t distribution acquisition unit 301 into a small particle group and a large particle group using a predetermined threshold, as shown in FIGS. 3A to 3C. As the predetermined threshold, for example, a particle size giving the minimum value of the frequency is set. Particles having a size smaller than a predetermined threshold are classified into the small particle group, and particles having a size larger than the predetermined threshold are classified into the large particle group.

The ratio calculation unit 303 shown in FIG. 1 calculates the value of the ratio between the number of particles belonging to the small particle group and the number of particles belonging to the large particle group. The value of the ratio may be the value of the ratio of the number of particles belonging to the large particle group to the number of particles belonging to the small particle group or may be the value of the ratio of the number of particles belonging to the small particle group to the number of particles belonging to the large particle group. Hereinafter, examples using the ratio of the number of particles belonging to the small particle group to the number of particles belonging to the large particle group will be described.

The survival rate determination unit 304 reads out the pre-acquired relationship between the ratio of the number of particles belonging to the small particle group to the number of particles belonging to the large particle group and the proportion of dead cells or living cells in a solution from the data storage device 401. The survival rate determination unit 304 calculates the proportion of dead cells or living cells in a solution based on the read-out relationship and the value of the ratio calculated by the ratio calculation unit 303 and determines the survival rate of the cultured cells. Herein, the survival rate of the cultured cells is, for example, the proportion of living cells relative to the total of dead cells and living cells. However, the survival rate of culture cells may be determined from the proportion of dead cells.

The arithmetic processor 300 may be connected to, for example, a temporary storage device 402, a signal output device 403, signal input device 404, a signal transmission/reception device 405, and a display 406. The temporary storage device 402 temporarily stores information in the calculation process by the arithmetic processor 300. The signal output device 403 outputs signals processed by the arithmetic processor 300. The signal input device 404 inputs signals to be processed by the arithmetic processor. The signal transmission/reception device 405 transmits and receives signals to and from an external device. The display 406 displays information in the processing by the arithmetic processor 300 and information on the results of the processing.

The cell survival rate determining device according to the first embodiment described above can determine the survival rate of cells without using a staining reagent and without depending on the autofluorescence of cells.

Second Embodiment

Figure 6:
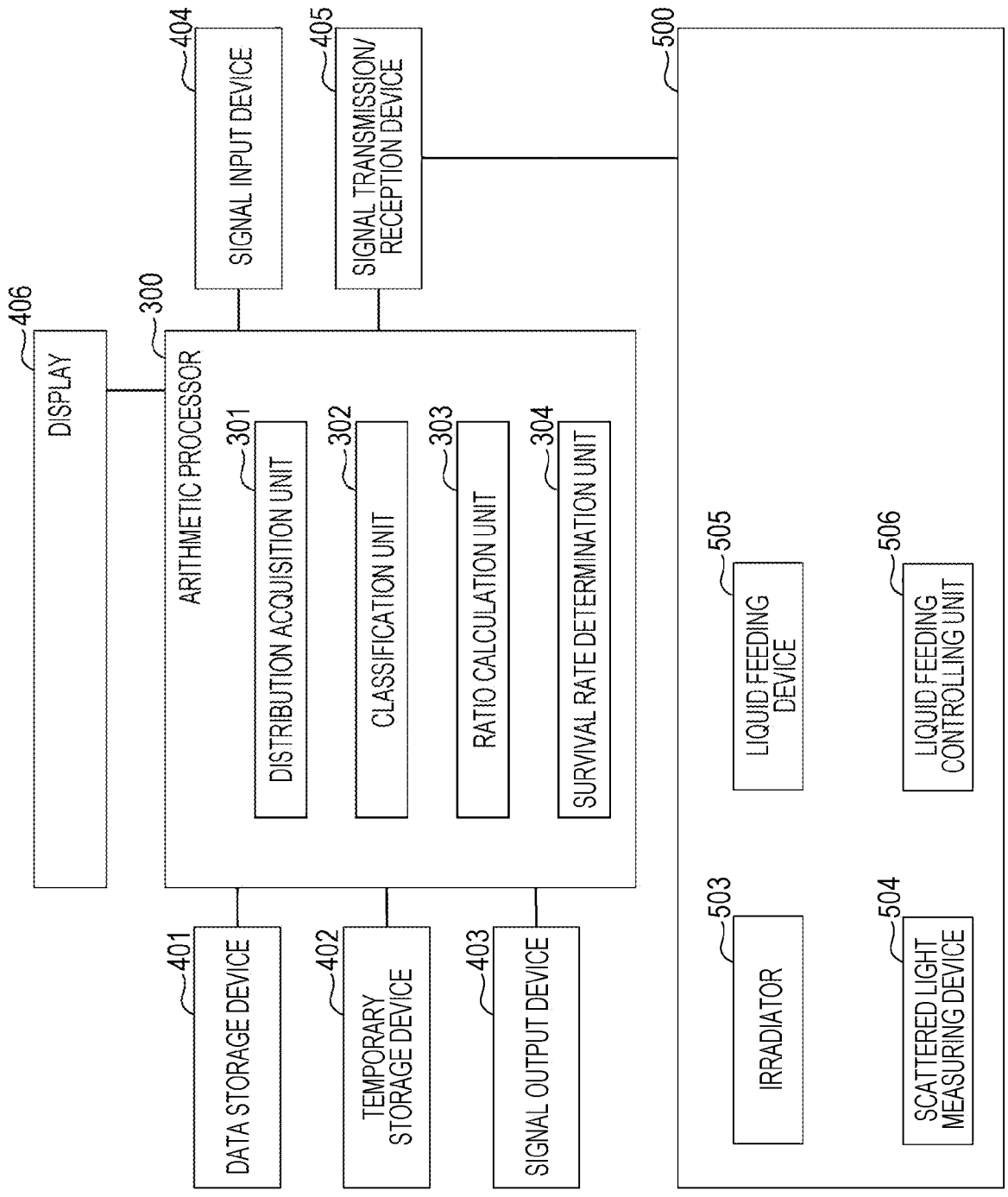
FIG. 6 is a schematic diagram of a cell survival rate determining device according to a second embodiment.
Figure 7:
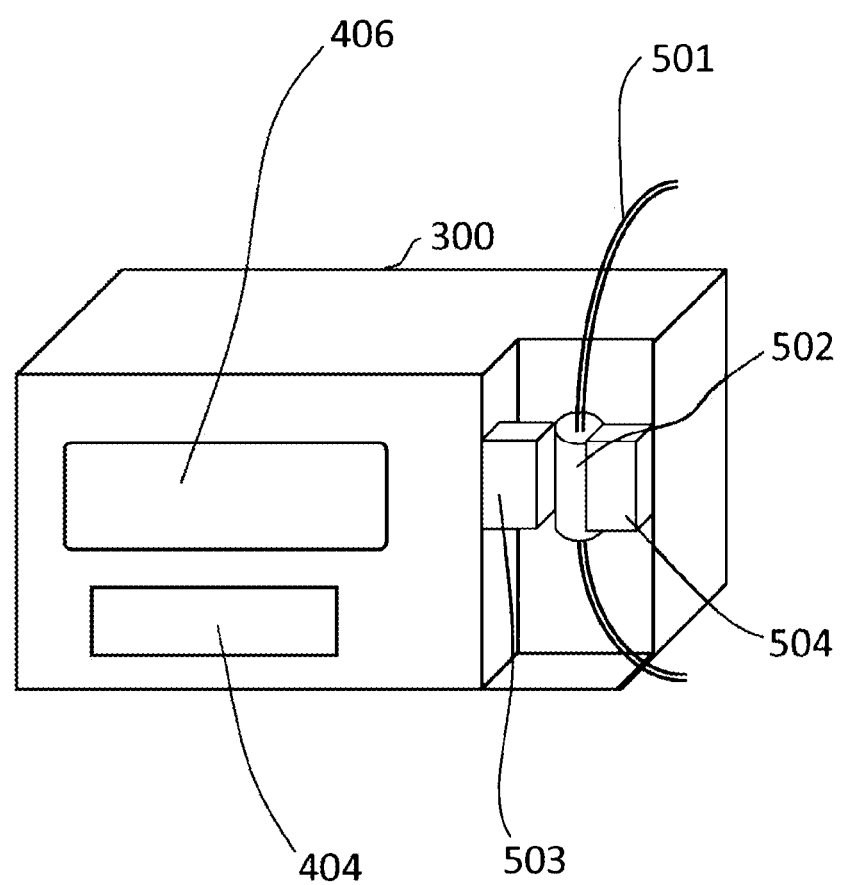
FIG. 7 is a schematic diagram of a cell survival rate determining device according to the second embodiment.
Figure 8:
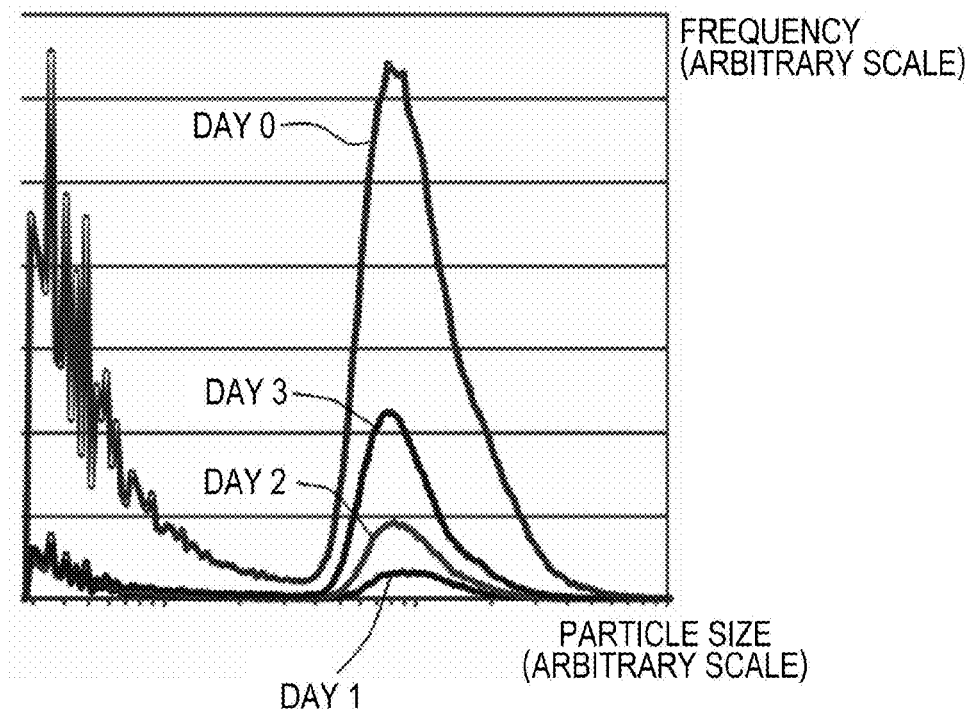
FIG. 8 is a graph showing frequency distributions of particles according to an example on Day 0 to Day 3 after the start of culture.
Figure 9:
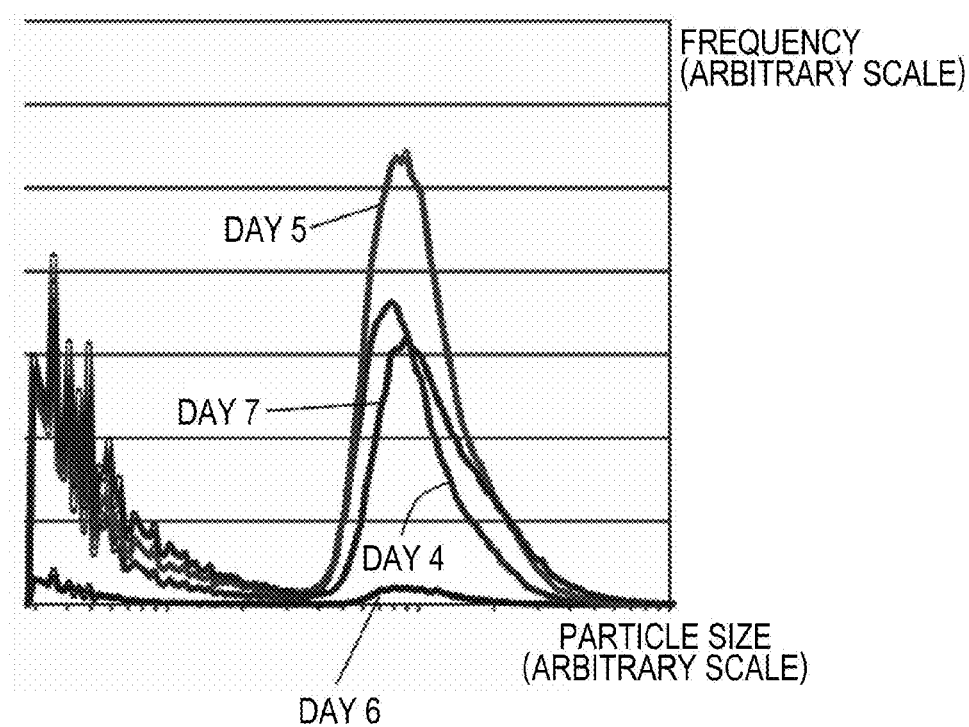
FIG. 9 is a graph showing frequency distributions of particles according to the example on Day 4 to Day 7 after the start of culture.
Figure 10:
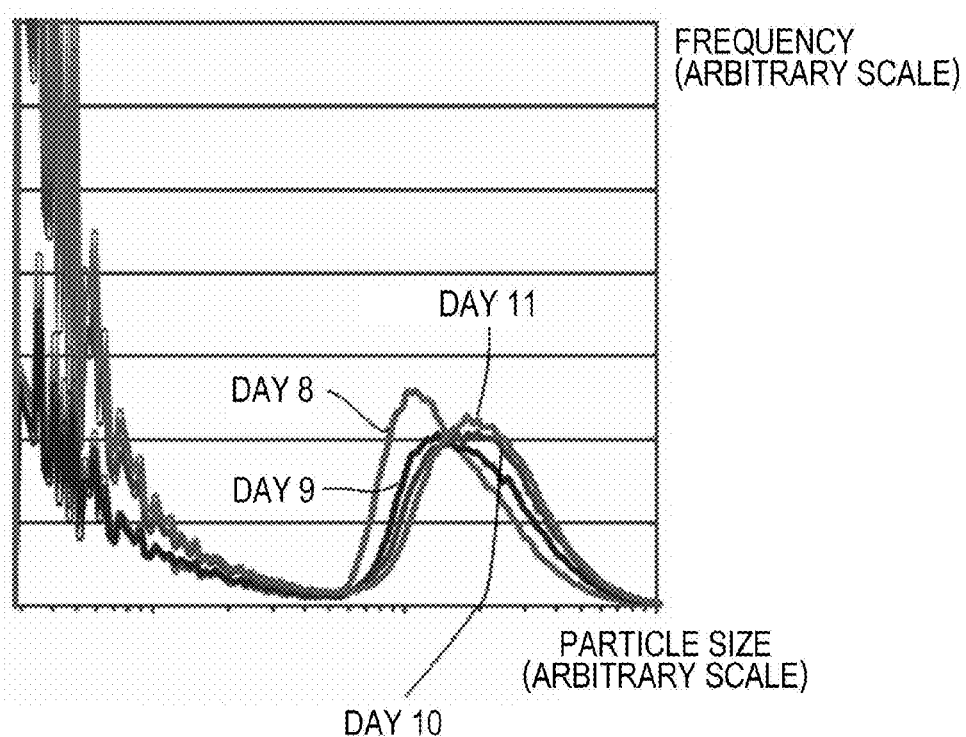
FIG. 10 is a graph showing frequency distributions of particles according to the example on Day 8 to Day 11 after the start of culture.
Figure 11:
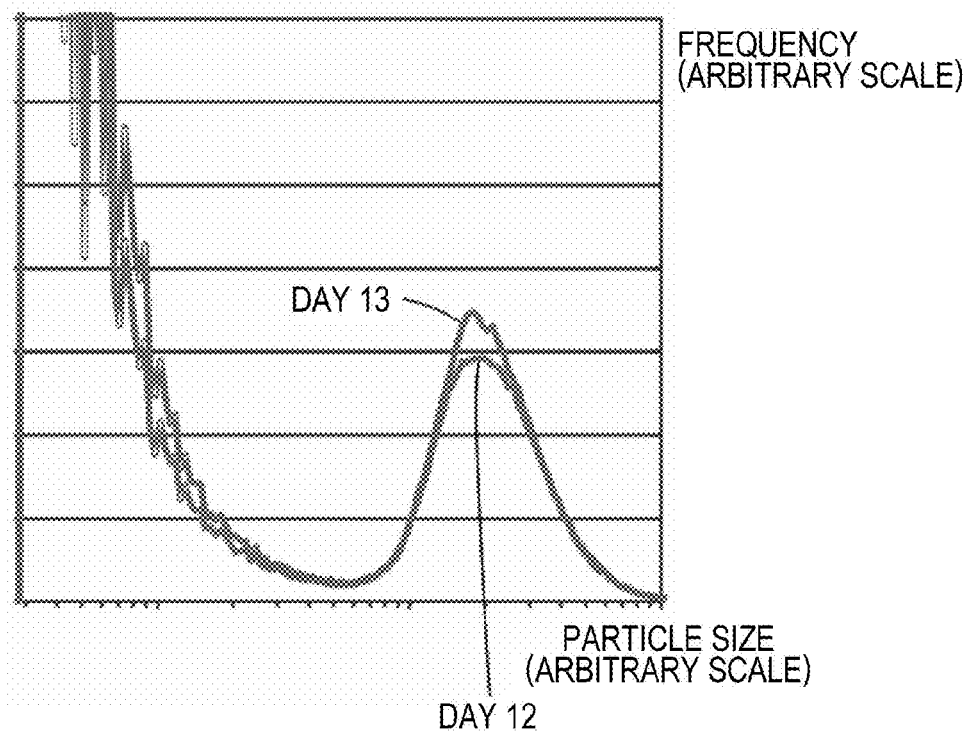
FIG. 11 is a graph showing frequency distributions of particles according to the example on Day 12 and Day 13 after the start of culture.

The cell survival rate determining device according to a second embodiment further includes an optical particle detector 500, as shown in FIGS. 6 and 7. The optical particle detector 500 includes, for example, a detachable flow channel 501 wherein a solution containing particles including cultured cells flows, a detachable measuring cuvette 502 connected to the flow channel 501, an irradiator 503 irradiating the inside of the measuring cuvette 502 with measurement light, and a scattered light measuring device 504 measuring the intensity of scattered light generated in the measuring cuvette 502 irradiated with the measurement light.

The solution containing particles including cultured cells flows in the flow channel 501 by means of a liquid feeding device 505. The liquid feeding device 505 is controlled by a liquid feeding controlling unit 506 to set, for example, the flow rate of the solution. The flow channel 501 can be detached from the optical particle detector 500. The detached flow channel 501 may be washed or may be replaced with a new clean flow channel 501. The measuring cuvette 502 is formed of a transparent material that is transmissive the measurement light and scattered light. Examples of the material of the measuring cuvette 502 include, but not limited to, quartz glass. The measuring cuvette 502 can be detached from the optical particle detector 500. The detached measuring cuvette 502 may be washed or may be replaced with a new clean measuring cuvette 502.

When the flow channel 501 and the measuring cuvette 502 are not clean, there is a risk that the particles measured last time remain in the flow channel 501 and the measuring cuvette 502 and affect the subsequent measurement. In contrast to this, since the flow channel 501 and the measuring cuvette 502 according to the second embodiment are detachable from the optical particle detector 500, it is easy to clean the flow channel 501 and the measuring cuvette 502.

The irradiator 503 includes, for example, a laser light source and a controller for the laser light source. The irradiator 503 irradiates the inside of the measuring cuvette 502 with measurement light, such as laser light. A lens may be arranged such that the measuring light focuses in the measuring cuvette 502. The irradiation of particles in the measuring cuvette 502 with measuring light generates Mie scattered light in the particles. The scattered light measuring device 504 measures the intensity of scattered light generated in the particles.

The intensity of scattered light measured with the scattered light measuring device 504 is transmitted to the distribution acquisition unit 301 via, for example, the signal transmission/reception device 405. As described above, since the intensity of the Mie scattered light reflects the size of particles, the distribution acquisition unit 301 acquires a particle size distribution based on the intensity of scattered light generated in each of the particles.

The other components of the cell survival rate determining device according to the second embodiment are the same as those in the first embodiment, and descriptions thereof are omitted.

Examples

A medium (CD OptiCHO, registered trademark, protein-free, animal-derived ingredient-free, manufactured by invitrogen) supplemented with L-glutamine (final concentration: 6 mmol/L) and Anti-Clumping Agent (final concentration: 1%) was prepared. CHO-K1 cells producing Trastuzumab were suspension-cultured in this medium at 37° C. in the presence of 5% $CO_2$. After the start of the suspension culture, the medium containing the cells was sampled on a regular basis.

The sampled medium was diluted at a predetermined rate, and the particles contained in the medium were each irradiated with laser light using a particle detector (IMD-W, manufactured by Azbil Corporation) to measure the intensity of Mie scattered light generated in each of the particles. The intensity of Mie scattered light generated in a particle represents the diameter of the particle. The cells contained in the sampled and diluted medium were stained with trypan blue, and the total number of the cells and the number of the stained cells were counted with a cell counter. The stained cells were determined to be dead cells. The survival rate of the cells was calculated from the result of the determination. The sampled and diluted medium was further photographed, and the particles in the medium were observed.

Figure 12:
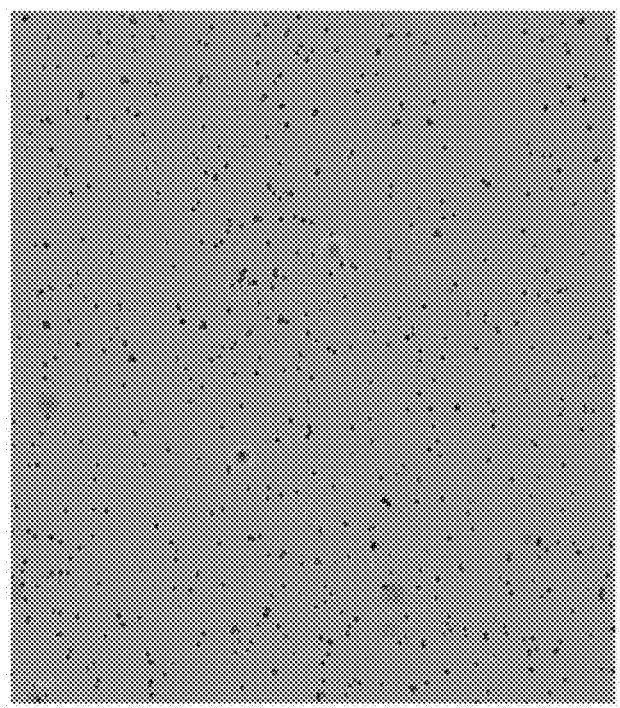
FIG. 12 is a photograph of a culture medium containing suspension-cultured cells according to the example.

FIGS. 8 to 11 are histograms each showing the frequency distribution of particle diameter measured every day after the start of the culture. In each histogram, a distribution of a small particle group and a distribution of a large particle group appeared with a particle diameter giving the minimum value of the frequency as the boundary. From the image of a sampled medium containing cells shown in FIG. 12, it was assumed that the particles classified into the large particle group include living cells.

Figure 13:
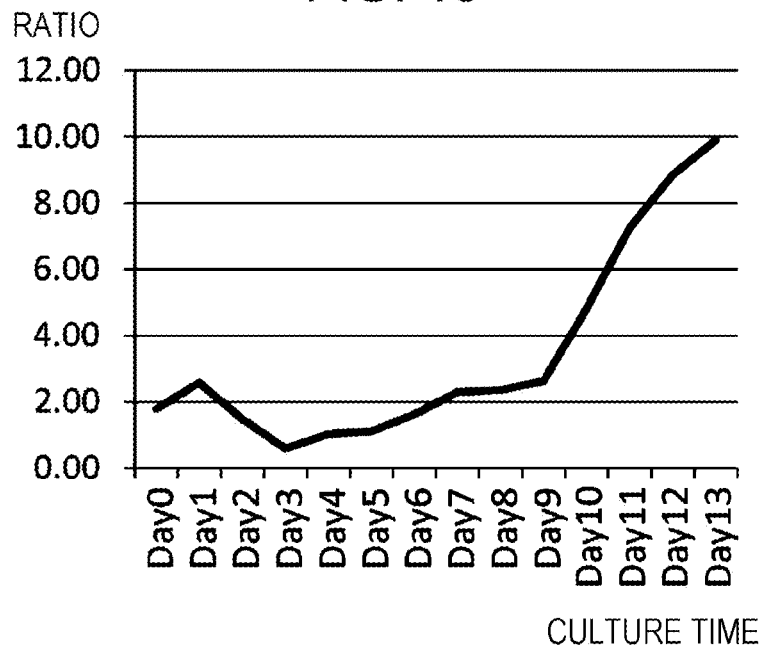
FIG. 13 is a graph showing a relationship between the culture time of the cells and the ratio of the number of particles belonging to the small particle group to the number of particles belonging to the large particle group according to the example.

FIG. 13 shows a graph obtained by plotting the value of the ratio of the number of particles belonging to the small particle group to the number of particles belonging to the large particle group with respect to the culture time. As shown in FIG. 13, the values of the ratio tended to increase with the number of days of culture. The reason why the value of the ratio at the initial stage of culture is somewhat large is probably that small particles previously measured remained in the particle detector. The value of the ratio then decreased once. This is probably caused by that living cells grew and particles to be classified into the large particle group increased.

Figure 14:
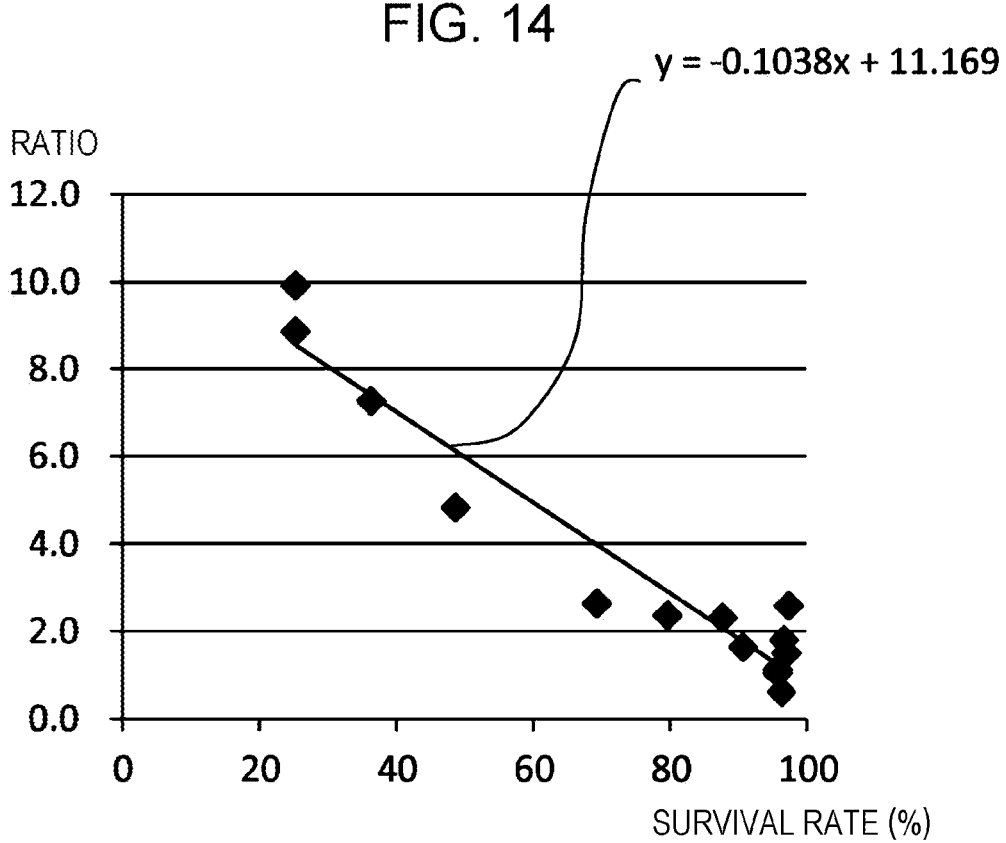
FIG. 14 is a graph showing a relationship between the survival rate of the cells and the ratio of the number of particles belonging to the small particle group to the number of particles belonging to the large particle group according to the example.

FIG. 14 shows a graph obtained by plotting the values of the ratio of the number of particles belonging to the small particle group to the number of particles belonging to the large particle group with respect to the survival rate of cells. A correlation was recognized between the ratio and the survival rate of cells. Accordingly, it was demonstrated that when cells are cultured, particles to be classified into the small particle group increase in the medium with the number of days of culture and that the survival rate of cells can be estimated from the ratio between the number of particles belonging to the small particle group and the number of particles belonging to the large particle group.

What is claimed is:

1. A cell survival rate determining device comprising:
   a distribution acquisition unit acquiring a particle size distribution in a solution containing particles including cultured cells;
   a classification unit classifying the particles into a small particle group and a large particle group using a predetermined threshold in the distribution;
   a ratio calculation unit calculating the value of a ratio between the number of particles belonging to the small particle group and the number of particles belonging to the large particle group; and
   a survival rate determination unit determining the survival rate of the cultured cells from the value of the ratio using a pre-acquired relationship between the ratio and cell survival rate.

2. The cell survival rate determining device according to claim 1, wherein the distribution acquisition unit acquires the particle size distribution based on an image of the solution.

3. The cell survival rate determining device according to claim 1, wherein the distribution acquisition unit acquires the particle size distribution based on the intensity of scattered light generated in each of the particles.

4. The cell survival rate determining device according to claim 3, further comprising:
   a detachable flow channel in which the solution flows;
   a detachable measuring cuvette connected to the flow channel;
   an irradiator irradiating the inside of the measuring cuvette with measurement light; and
   a scattered light measuring device measuring the intensity of scattered light generated in the measuring cuvette irradiated with the measurement light.

5. The cell survival rate determining device according to claim 1, wherein the cultured cells are suspension-cultured.

6. The cell survival rate determining device according to claim 1, wherein the cultured cells are Chinese hamster ovary (CHO) cells.

7. A cell survival rate determining method comprising:
   acquiring a particle size distribution in a solution containing particles including cultured cells;
   classifying the particles into a small particle group and a large particle group using a predetermined threshold in the distribution;
   calculating the value of a ratio between the number of particles belonging to the small particle group and the number of particles belonging to the large particle group; and
   determining the survival rate of the cultured cells from the value of the ratio using a pre-acquired relationship between the ratio and cell survival rate.

8. The cell survival rate determining method according to claim 7, wherein the particle size distribution is acquired based on an image of the solution.

9. The cell survival rate determining method according to claim 7, wherein the particle size distribution is acquired based on the intensity of scattered light generated in each of the particles.

10. The cell survival rate determining method according to claim 7, wherein the cultured cells are suspension-cultured.

\* \* \* \* \*